United States Patent [19]

Bostick

[11] 4,197,849

[45] Apr. 15, 1980

[54] FLEXIBLE MANIPULATIVE INCONTINENT AID

[76] Inventor: Emma T. Bostick, 6525 Calle Lottie, Tucson, Ariz. 85718

[21] Appl. No.: 838,623

[22] Filed: Oct. 3, 1977

[51] Int. Cl.$^2$ ............................................. A61F 5/44
[52] U.S. Cl. ................................. 128/295; 128/760; 4/144.3
[58] Field of Search .............. 128/295, 294, 283, 2 F, 128/760, 764, 767, 771; 150/9; 229/62.5; 4/144.1, 144.2, 144.3, 144.4; 116/114 AM

[56] References Cited

U.S. PATENT DOCUMENTS

| Re. 29,319 | 7/1977 | Nordby | 128/283 |
|---|---|---|---|
| 2,024,341 | 12/1935 | De Graff | 128/295 |
| 2,445,220 | 7/1948 | Isaacson | 128/295 |
| 2,741,247 | 4/1956 | Marsan | 128/283 |
| 2,837,095 | 6/1958 | Stevenson | 128/283 |
| 3,081,771 | 3/1963 | Lee | 128/283 |
| 3,383,030 | 5/1968 | Downey | 229/62.5 |
| 3,613,123 | 10/1971 | Langstrom | 128/295 |
| 3,675,654 | 7/1972 | Baker et al. | 128/287 |
| 3,918,433 | 11/1975 | Fuisz | 128/295 |

*Primary Examiner*—Robert W. Michell
*Assistant Examiner*—J. L. Kruter
*Attorney, Agent, or Firm*—Gregory J. Nelson

[57] ABSTRACT

An incontinent aid primarily for male patients including an outer receptacle of pliable liquid-impervious material. The front panel of the receptacle is provided with an adhesive section for attachment to the pubic area. A portion of the receptacle bounded by the adhesive portion is formed having tabular projections which can be inwardly deflected and secured about the male penis. The rear side of the receptacle has a closable opening for access during the fitting procedure. The interior of the receptacle is lined with an absorbent material. In another embodiment, the receptacle may include a viewable chemically reactive strip for giving a visual indication of the pH or other characteristics of the patients urine.

8 Claims, 13 Drawing Figures

FLEXIBLE MANIPULATIVE INCONTINENT AID

The present invention relates to a device for collecting body fluids and more particularly relates to an incontinent aid of the type adapted to be placed in contact with the urogenic member of a male patient. The receptacle consists of a pliable liquid-impervious bag having an opening for receiving the urogenic member and containing an appropriate absorbent material.

The collection and retention of urine from incontinent patients is a problem in hospitals, nursing homes and for those receiving home care. The urine must be collected in an efficient and sanitary manner for the comfort of the patient and to avoid infection, irritation and other problems. One common method is to provide receptacles for the collection of urine. These vessels must be supplied to the patient at each occasion of use and thereafter must be emptied, cleaned and also sterilized. It is also common to provide an absorbent pad or lining which when worn by the patient is secured in place by plastic underpants. The absorbent lining material must be changed regularly and generally can be worn only for a short period of time. Further, the absorbent material, once it becomes wet, it is in contact with the patient's skin and can cause infection and irritation.

Another approach to the problem of incontinence has been to provide devices which are generally called catheters. These devices generally include a catheter or sheath which fits within or about the urogenic member and a tube and reservoir. The device may be designed for ambulatory patients and include appropriate waist band or straps, which can be secured to the patient. The disadvantage with these devices is they are cumbersome, bulky and uncomfortable for the patient to use.

Still another approach to the problem is to provide plastic bags as receptacles which can be in the form of an elongated bag having an opening. The bag may include an appropriate absorbent material and be provided with hooks or some type of adhesive material on the exterior side which serves as attachments for a girdle or suspensatory. Devices of this type are shown in U.S. Pat. Nos. 3,295,145 and 3,613,213. The disadvantage of devices of this type is that they may leak around the opening, causing discomfort to the patient.

The present invention is an improved collection receptacle or device for urine, especially designed for use by the male incontinent patient. The device includes an outer receptacle of liquid-impervious material such as vinyl or polyethylene film. One side of the receptacle carries an adhesive ring having a stripable facing cover which is removed at the time of use. Within the ring are tabular projections which are adapted to be bent inwardly about the penis and secured in place by adhesive tape. An opening is provided in the receptacle opposite the tabs to permit access to the interior of the bag for the taping procedure. The opening may be closed by an appropriate strip of adhesive tape placed adjacent the opening. The interior of the bag is filled with appropriate absorbent material, such as cotton, foam plastic, such as polyuretane or any other material suitable for absorbing liquid. In other embodiments of the present invention, the receptacle is contoured to conform to the anatomy of the user and may include straps or adhesive tabs which may be secured to the body of the user. In still another embodiment, the bag may be secured to the penis by a prophylactic type of seal.

The above and other objects and advantages fo the present invention will become more apparent from the following description and drawings in which.

Figure 1:
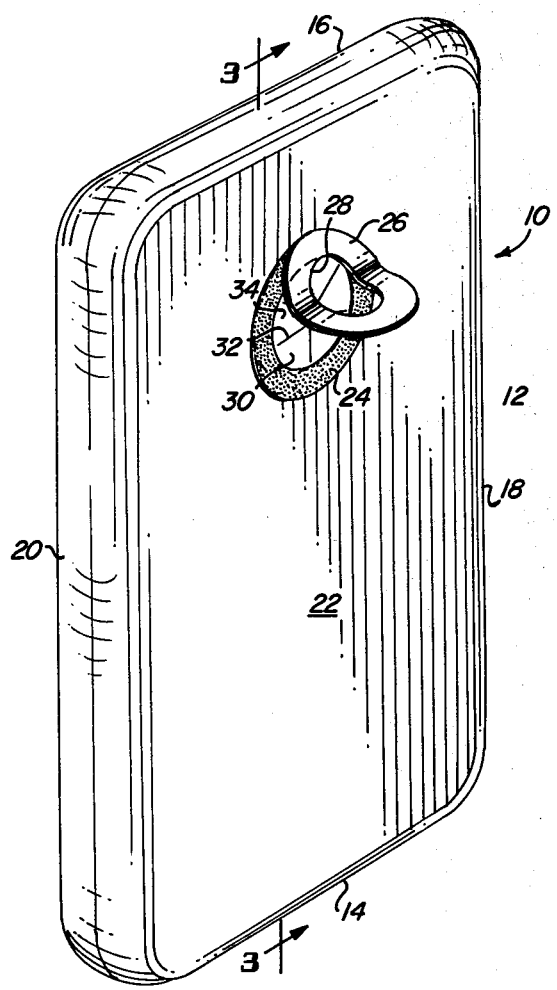
FIG. 1 is a front perspective view of the incontinent aid of the present invention.

Refering now to the drawings, FIGS. 1–5 illustrate the incontinent aid of the present invention which is generally designated by the numeral 10. The incontinent aid includes an outer receptacle or bag 12 which is shown as generally rectangular and is formed from a pliable, liquid-impervious material such as, a vinyl film, polyethylene film or a coated paper appropriately sealed at opposite ends 14 and 16 and sides 18 and 20 to make the receptacle water tight. Typically, for an adult patient, the receptacle would measure approximately 6" wide by 16" in length. Size may vary and pediatric sizes are generally smaller. The incontinent aid shown in FIGS. 1–5 is designed for use primarily by male patients. Secured to the outer surface of the front panel 22 of the bag, spaced about one-third of the length of the bag from the top side 14 is an annular ring of adhesive material 24, covered by an appropriate peel patch 26. When the peel patch 26 is removed the adhesive can be secured to the genital area of the user as will be described. The adhesive material 24 and the peel patch have been shown as being annular, but may be any shape, such as square, defining a central opening 28 exposing a portion 30 of the front panel of the bag. Material section 30 within the opening 28 is provided with a plurality of intersecting slits or perforations 32 forming a plurality of generally triangular tabs 34. Tabs 34 can be bent inwardly and secured to the male patient as will be explained. Note the particular shape of the tabular members 34 may be varied.

Figure 2:
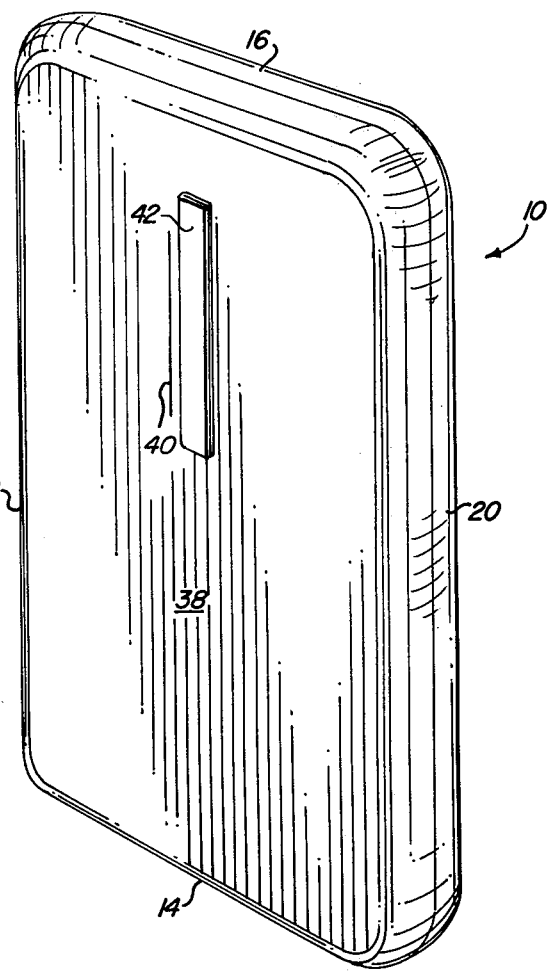
FIG. 2 is a rear perspective view of the incontinent aid of the present invention.
Figure 4A:
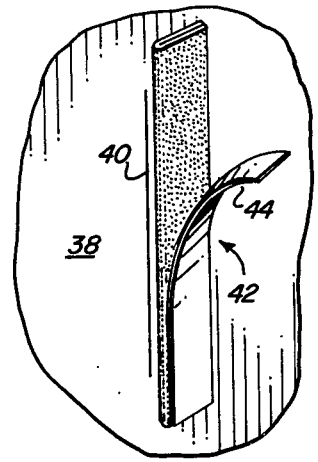
FIG. 4A is a detail view of the sealing member on the rear of the device in an open position.
Figure 4B:
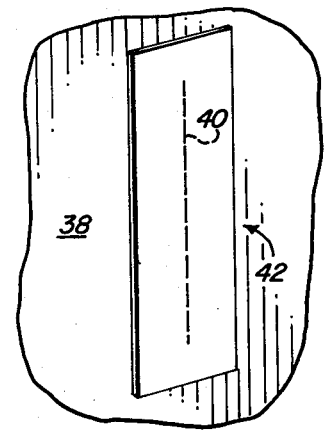
FIG. 4B is a detail view of the sealing member on the rear of the device in a closed position.
Figure 5:
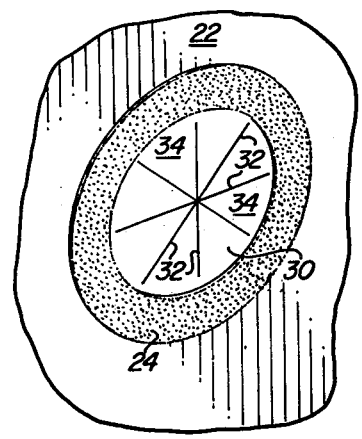
FIG. 5 is a detail view of the adhesive member on the front of the incontinent aid.

The rear panel of the bag as shown in FIG. 2 is generally designated by the numeral 38. Rear panel 38 is provided with a medial slit 40 which is located generally opposite tabs 34 on the front panel 22. An adhesive flap 42 is positioned adjacent opening 40 and is generally coincident with opening 40. A peelable facing 44 covers adhesive flap 42. Peelable facing 44 may be removed from adhesive flap 42 and opening 40 closed by folding adhesive flap 42 over the opening as best seen in FIGS. 4A and 4B.

Figure 3:
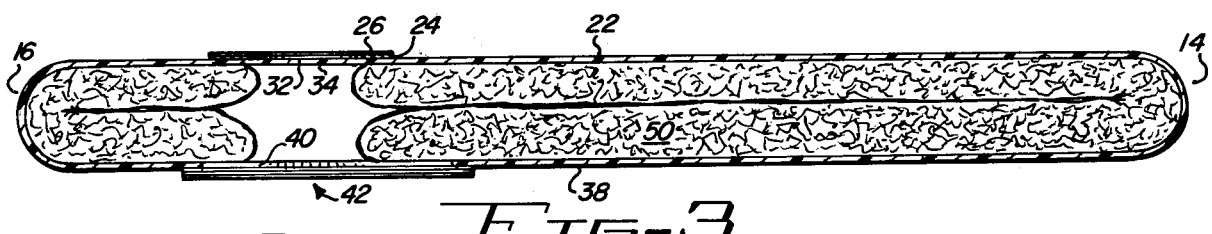
FIG. 3 is a sectional view taken along lines 3—3 of FIG. 1.

Refering to FIG. 3, the outer receptacle 12 defines an interior space 50 which is substantially filled with an appropriate absorbent material except in the area extending between the opening 40 and the tabs 34. The absorbent material may be selected from a variety of materials, such as cellulose wadding, foam plastic, appropriately treated paper, or cotton. The absorbent material may be simply packed in the interior space 50 of the receptacle 12 or preferably is adhesively or otherwise secured to the inner surface of the receptacle.

Figure 6A:
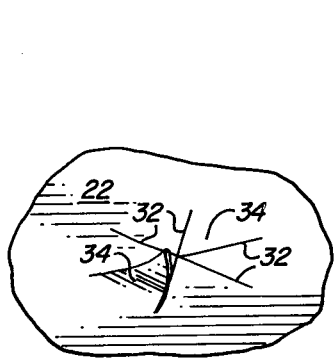
FIGS. 6A to 6C illustrate the fitting procedures as applied to a male patient viewed from the interior of the receptacle.
Figure 6B:
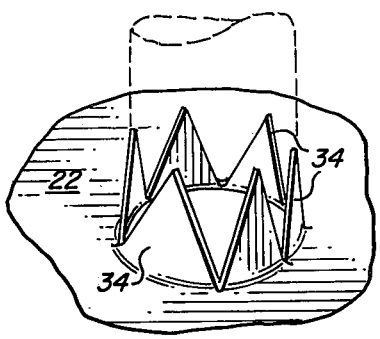
Figure 6C:
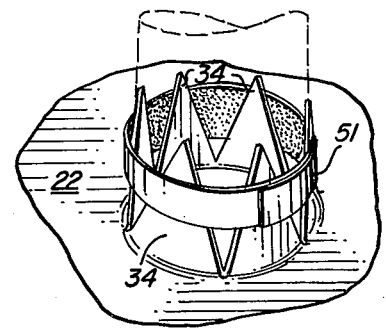

A better understanding of the present invention will be had from the following description of the manner in which the receptacle is secured to a patient. FIGS. 6A to 6C illustrate the attachment of the receptacle 10 to a male patient. The patient is generally placed in a prone position on his back when the receptacle 12 is attached to the patient. The peelable strip 26 is removed from the adhesive ring 24. Tabs 34 are depressed inwardly as shown and the male penis is inserted in the opening defined by the tabs 34 with the tabs extending along the penis. Access to the interior of the bag is through opening 40 in the rear panel 38. The nurse or attendant can place medical tape 51, preferably of the type sold under the tradenames "Micropore" and "Blenderm" around the inwardly depending tabs 34 and in this way secure the tab to the penis to provide a watertight seal against leakage from the interior of the bag. The adhesive ring 24 is firmly pressed against the pubic area of the user to secure the receptacle in place. When this is completed, as shown in FIGS. 4A and 4B, the peelable strip 44 is removed from adhesive flap 42 and flap 42 folds over to close opening 40. This makes the entire unit watertight so that no leakage will take place from the bag. The bag can be worn by the incontinent patient for varying periods, depending on the patient. Hospital testing has indicated that the typical incontinent patient can wear the device of the present invention for substantial periods without change being required. For example, the average patient can wear the incontinent device of the present invention for overnight without the necessity of a change. The tab seals around the penis and adhesive ring secured to the pubic area of the user effectively prevents any leakage of urine from the bag so that irritation and discomfort to the patient is minimized. When the bag is to be removed, the tape strip 42 at the rear side 38 of the bag is loosened to permit access to the interior of the bag. The tape around the penis is removed and the entire bag can be resealed and disposed of in a sanitary manner.

Figure 7:
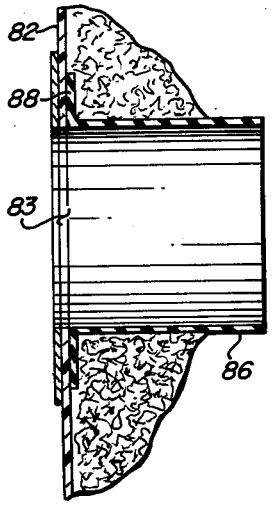
FIG. 7 is a detail view illustrating another means of attaching the aid to a male patient.
Figure 8:
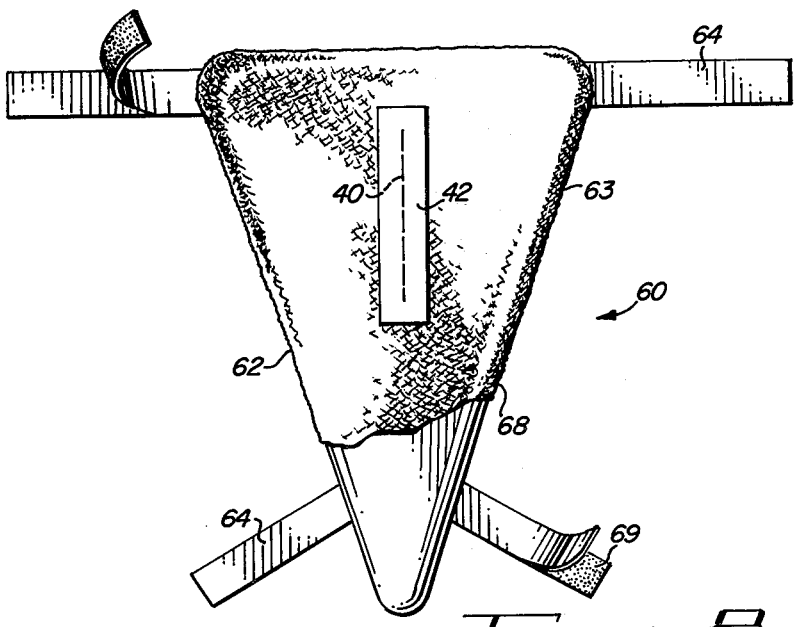
FIG. 8 is a front view of another embodiment of the incontinent aid of the present invention.
Figure 9:
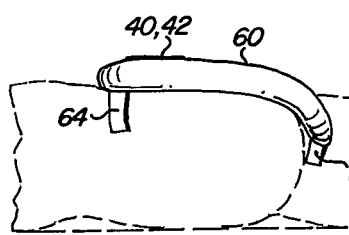
FIG. 9 shows the embodiment of FIG. 8 in place on a patient.

FIG. 8 illustrates an alternate embodiment of the present invention. The embodiment of FIG. 8 is generally indicated by the numeral 60 and is shown having a generally triangular shape to conform to the anatomy of the user. The incontinent aid 60 is constructed generally as has been described with reference to FIGS. 1-3, except that the opposite side 62 and 63 converge in a generally triangular shape so the bag can be positioned in the perineal area. Tabs or straps 64 may be secured to opposite side 62 and 63 of the receptacle 60. Straps 64 may be tied about the waist of the user after the aid is positioned or may be provided with an adhesive surface 69 and taped to the abdominal and leg areas of the patient as illustrated in FIG. 7. Other shapes may also be utilized, such as, an hourglass configuration. The receptacle 60 is insulated with a layer of material 68 which may be a treated paper product covering the receptacle. The insulation layer is for additional patient comfort.

Figure 10:
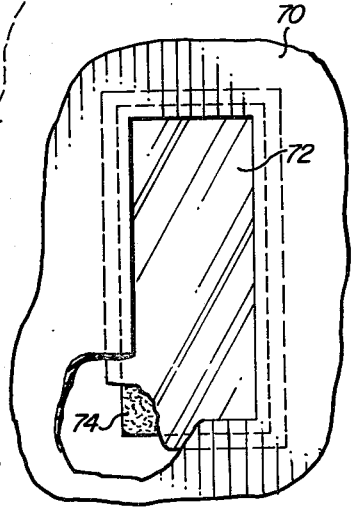
FIG. 10 is a detail view showing inclusion of means for testing chemical characteristics of collected liquids.

FIG. 10 shows another feature of the present invention. In FIG. 10 a portion of the front surface of the receptacle as shown in either FIG. 1 or 8 is illustrated and is generally designated by the numeral 70. Front panel 70 is provided with a transparent insert 72. An appropriate chemically reactive strip 74 is positioned below the transparent insert 72 within the interior of the incontinent aid. Chemically reactive strip 74 may be a litmus paper or other type indicator for measuring or determining the characteristics of urine as pH, sugar and similar characteristics are often monitored by medical personnel. The chemically reactive strip would, for example,, change color and give medical personnel a ready indication of the desired characteristics.

FIG. 7 shows another embodiment of the present invention generally designated by the numeral 80. Refering to FIG. 7 the incontinent aid shown in this embodiment includes a top panel 82 which defines an opening or aperture 83 on the upper surface. A sheath of elastomeric material 86 is secured at the opening 83 by a weld, adhesive or dialectric method along annular flange 88. Sheath 86 depends inwardly to the interior of the incontinent aid and may be of natural rubber and is constructed similar to a prophylactic. The sheath 86 is adapted to engage the male penis in sealing relationship. In other respects, the embodiment shown in FIG. 7 is similar to the embodiments described above.

From the foregoing, it will be seen that the present invention provides a convenient incontinent aid which is designed primarily for use by male patients. The incontinent aid of the present invention can be easily secured to the patient and prevents or minimizes leakage which can cause irritation and is uncomfortable for the patient. The incontinent aid of the present invention can be made in various sizes and shapes in accordance with the anatomy of the patient, as for example, in adult and pediatric sizes. Hospital tests have shown that the incontinent aid of the present invention can be worn for substantially longer times than conventional incontinent aids, thus, minimizing the time required by hospital personnel in changing and replacing the aids. The aid can also be provided with an integrally formed chemically reactive element which serves as an indication of the chemical characteristics. The receptacle is disposable after use. The receptacle can also be used as a diaper for young children.

From the foregoing, it will be obvious that the invention is of simple construction which can be readily implemented from a variety of well known, conveniently available materials to provide a highly efficient incontinent aid. Various changes and alterations and modifications will be apparent to those skilled in the art. To the extent that these various modifications do not depart from the spirit and scope of the invention as set forth in the accompanying claims, they are intended to be encompassed therein.

I claim:
1. A male incontinent device comprising:
   (a) A receptacle of pliable, liquid-impervious material having a front panel, a rear panel, said panels connected to each other to define a liquidtight compartment therebetween;
   (b) said front panel having means for securement about the male penis including projection means adapted to extend inwardly into the compartment and further adapted to be engaged about the shaft of penis to provide a seal thereabout;
   (c) a sealable access opening leading into the compartment and positioned on the rear panel opposite to said projection means, said access opening being sized so an attendant may reach therethrough into the compartment to seal the projection means to the penis;

(d) liquid absorbent means within said compartment in unobstructing relation to the portion of the compartment between the access opening and the projection means, and;

(e) means on the rear panel adjacent the sealable opening to provide a means for sealing said access opening after the device has been positioned.

2. The incontinent device of claim 1 further including an adhesive portion positioned adjacent said projection means and adapted to secure the incontinent aid to the user.

3. The incontinent aid of claim 2 wherein said projection means comprise tabs formed in the front panel of said receptacle which are adapted to be secured to the penis by adhesive means.

4. The incontinent aid of claim 2 wherein one of said panels includes a viewable chemically reactive material for giving an indication of a characteristic of the patient's urine.

5. The incontinent aid of claim 2 wherein said panels are provided with an insulative covering.

6. The incontinent aid of claim 2 wherein said projection means comprises an elastomeric sheath secured to said panel.

7. The incontinet aid of claim 6 wherein said receptacle is of a shape to conform to the anatomy of the wearer.

8. The incontinent aid of claim 7 further including tie means for securing incontinent aid to the body of the user.

* * * * *